(12) United States Patent
Obata et al.

(10) Patent No.: US 6,444,239 B2
(45) Date of Patent: Sep. 3, 2002

(54) PROCESS FOR PRODUCING ISOFLAVONE AGLYCONE-CONTAINING COMPOSITION

(75) Inventors: Akio Obata; Tatuo Manaka; Koichiro Tobe; Toru Izumi; Makoto Saito; Mamoru Kikuchi, all of Chiba (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/768,595

(22) Filed: Jan. 25, 2001

(30) Foreign Application Priority Data

Jan. 28, 2000 (JP) .......................................... 2000-20393

(51) Int. Cl.7 .............................................. A61K 35/78
(52) U.S. Cl. .......................... 424/757; 426/46; 530/378
(58) Field of Search ........................... 435/18, 23, 68.1, 435/272; 424/725, 757, 195.1; 426/46, 598, 629, 634; 530/378; 549/403

(56) References Cited

U.S. PATENT DOCUMENTS

| 5,100,679 A | * | 3/1992 | Delrue .......................... 426/44 |
| 5,827,682 A | * | 10/1998 | Bryan et al. ................. 435/68.1 |
| 5,885,632 A | * | 3/1999 | Takebe et al. .................. 426/40 |
| 6,015,785 A | * | 1/2000 | Shen et al. ...................... 514/2 |
| 6,303,161 B1 | * | 10/2001 | Takebe et al. ................. 426/46 |

FOREIGN PATENT DOCUMENTS

| JP | 62-126186 | | 6/1987 |
| JP | 5-170756 | | 7/1993 |
| JP | WO 97/37549 | * | 10/1997 |
| JP | 11-89589 | * | 4/1999 |
| WO | WO 95/10512 | * | 4/1995 |

OTHER PUBLICATIONS

Matsuura M. Studies on Beta Glucosidases from Soybeans . . . Biosci Biotech Biochem 59(9) 1623–1627, 1995.*
Peterson G. Genistein Inhibition of the Growth of Human Breast Cancer Cells . . . Biochem and Biophys Res Comm. 179(1)661–667. Aug. 30, 1991.*
Matsuura M. Beta Glucosidases From Soybeans Hydrolyze Daidzin and Genistin. J of Food Science 58(1)144–147, 1993.*
Peterson et al. *Biochemical and Biophysical Research Communications*, vol. 179, No. 1, pp. 661–667 Aug. 30, 1991.
Yanagihara et al. *Cancer Research*, vol. 53, pp. 5815–5821, Dec. 1, 1993.

* cited by examiner

*Primary Examiner*—Ralph Gitomer
(74) *Attorney, Agent, or Firm*—Young & Thompson

(57) ABSTRACT

An isoflavone aglycone-containing composition having genistein as a main aglycone is produced by a process comprising allowing a protease and β-glucosidase to act on a soy protein raw material, an extract of a soy protein raw material or a by-product of a soy protein raw material to water-solubilize the protein of soybean origin and to convert isoflavone glycosides to the corresponding aglycones, separating water-soluble components from the enzymatic reaction mixture, and recovering water-insoluble matter.

10 Claims, No Drawings

PROCESS FOR PRODUCING ISOFLAVONE AGLYCONE-CONTAINING COMPOSITION

BACKGROUND OF THE INVENTION

1. Field of the Invention

The present invention relates to a process for obtaining a composition containing soybean isoflavone aglycones mainly comprising genistein.

2. Description of the Related Art

Isoflavone compounds, such as malonyldaidzin, malonylglycitin, malonylgenistin, daidzin, glycitin, genistin, daidzein, glycitein, and genistein, are known to have estrogenic activity, antioxidative activity, antibacterial activity, antilipemia activity, anticholesterol activity, and the like. In recent years, cancer cell differentiation and induction activity, oncogene inhibitory activity, and prophylactic activity on cancers have been confirmed. Thus, the usefulness of these isoflavone compounds has been attracting attention. Many researches have revealed that the pharmacological effects, such a cancer prophylactic effect, of isoflavone compounds are primarily attributed not to the glycosides themselves but their aglycones, such as daidzein or genistein. Of the soybean isoflavone aglycones genistein has recently been proved particularly excellent in physiological activities, including antiosteoporosis activity, antiarteriosclerotic activity, and anticancer activities in the breast, the stomach and the prostate (see M. Numoto, *Cancer Research*, vol. 53, p. 5815 (1993) and S. Barnes, *Biochem. Biophys. Res. Commun.*, vol. 179, p. 661 (1991).

Methods of obtaining isoflavone compounds include the methods described in Japanese Patent Laid-Open Nos. 62-126186 and 11-89589, for example. Since 95% or more of isoflavone compounds in soybeans are present in the form of glycosides, however, the isoflavone compounds obtained by the former method mainly comprise glycosides with little amount of aglycones. Further, the isoflavone aglycones obtained by the latter method, which uses soybean hypocotyl tissue as a raw material, mainly comprise daidzein with the genistein content being about ⅙ of daidzein.

The inventors of the present invention previously applied for a patent based on their findings that soy sauce cake and soy sauce oil, which are by-produced in soy sauce production, contain isofalvone compounds substantially comprising aglycones such as daidzein and genistein and that these aglycones can be obtained efficiently by organic solvent extraction (see Japanese Patent Laid-Open No. 5-170756). The problems associated with this method, however, are that the yield of aglycones is low, the raw materials are uncommon, and a special extraction operation is needed.

SUMMARY OF THE INVENTION

The present inventors have conducted extensive investigations on production of isoflavone aglycones from soybeans and found as a result that a composition containing isoflavone aglycones the majority of which is genistein can easily be obtained by allowing an enzyme preparation having protease activity and β-glucosidase activity to thoroughly act on a soybean raw material that is easily available in the market and recovering water-insoluble matter.

Having been completed based on the above finding, the present invention provides a process for producing an isoflavone aglycone-containing composition comprising allowing a protease and β-glucosidase to act on a soy protein raw material, an extract of a soy protein raw material or a by-product of a soy protein raw material to water-solubilize the protein of soybean origin and to convert isoflavone glycosides to the corresponding aglycones, separating water-soluble components from the enzymatic reaction mixture, and recovering water-insoluble matter. The majority of the aglycones present in the resulting composition is genistein.

According to the present invention, a composition containing isoflavone aglycones mainly comprising genistein can be obtained from an easily commercially available raw material through an easy and simple operation.

DETAILED DESCRIPTION OF THE INVENTION

The raw material used in the present invention is a soy protein raw material, an extract of a soy protein raw material or a by-product of a soy protein raw material. The soy protein raw material includes whole soybeans, dehulled soybeans, and defatted soybeans. The extract of a soy protein raw material includes a soy protein isolate, a soy protein concentrate, soybean milk, and a soybean extract containing isoflavone glycosides. The by-product of a soy protein raw material includes soybean molasses, soybean whey, and soybean curd waste. To help a protease enzyme act, it is preferred that these raw materials be previously heat treated to denature the protein and deactivate the trypsin inhibitor. The heat treatment is preferably carried out at 80 to 200° C. for about 10 to 60 minutes.

The enzymes which can be used in the present invention, i.e., a protease and glucosidase, can be crude enzymes as produced by culturing microorganisms or commercially available crude enzymes, such as protease preparations. The crude enzymes may be used as concentrated or purified by ultrafiltration or column chromatography. While not limiting, the amounts of the enzymes (protease and β-glucosidase) preferably range from 0.1 to 10 parts by weight in terms of the solid content per 100 parts by weight of the soybean raw material.

The enzymes (protease and β-glucosidase) are preferably of acid species whose optimum pH is in a range of from 2.0 to 6.0 and of thermostable species whose optimum temperature is 50° C. or higher.

Any commercially available crude enzymes can be used as long as they have protease activity and β-glucosidase activity. Enzyme preparations of the genus Penicilliuni or Aspergillus origin are preferred. Analysis of β-glucosidase activity on various commercially available protease preparations by the method of Ebata, el al. (*Nippon Nogeikagaku Kaishi*, vol. 46, p. 323 (1972)) revealed that those of Penicillium or Aspergillits origin, especially those having an optimum pH in an acidic region (acid protease preparations) exhibit high activity. Specific examples of preferred commercial enzyme preparations having both protease activity (PA) and β-glucosidase activity (GA) are Molsin F (PA: 38,000 U/g; GA: 260 U/g; available from Kikkoman Corp.), Sumizyme FP (PA: 50,000 U/g; GA: 172 U/g; available from Shin-nihon Kagaku Kogyo K.K.), Protease M Amano (PA: 5,500 U/g; GA: 132 U/g; available from Amano Pharmaceutical Co., Ltd.), Miso Koso Amano Al (PA: 3,000 U/g; GA: 28 U/g; available from Amano Pharmaceutical Co., Ltd.), AO Protease (PA: 24,000 U/g; GA: 20 U/g; available from Kikkoman Corp.), and IP Koso (PA: 34,000 U/g; GA: 4 U/g; available from Kikkoman Corp.). These enzyme preparations are sold as enzymes for food so that their safety as food has been established.

Of these enzyme preparations those having a protease activity of 5,000 U/g or more (as determined by the method described in P. E. Wilcox, *Methods Enzymol., vol.* 19, pp. 64–80 (1970)) and a β-glucosidase activity of 100 U/g or more (as determined by the method described in J. Ebata et al., *Nippon Nogeikagaku Kaishi,* pp. 323–329 (1972)) are preferred.

The manner of carrying out the enzymatic reaction is not particularly restricted. For example, the soybean raw material is added to a previously prepared aqueous dispersion of the enzyme preparation followed by stirring, or the aqueous enzyme dispersion is sprayed directly on the soybean raw material, or the enzyme preparation is added to a mixture of the soybean raw material and water, followed by stirring, or enzymes (protease and β-glucosidase) are brought into contact with the soybean raw material to impregnate. While the amount of water added is not particularly limited, too much water requires of necessity larger equipment to increase the cost and to reduce the productivity. A preferred amount of water is about 50 to 10,000 parts by weight per 100 parts by weight of the soybean raw material.

The enzyme reaction conditions, while not particularly limited unless abrupt deactivation of the enzymes or putrefaction by bacteria occurs, are preferably 40 to 70° C. and 1 to 24 hours. Since isoflavone glycosides are sparingly soluble in water, it is preferred to add an organic solvent to the reaction system in an amount of 1 to 50% by weight or to use thermostable enzymes to allow the reaction to be conducted at an increased temperature of 60 to 70° C. By such manipulations, the solubility of the isoflavone glycosides increases, and contamination with bacteria can be suppressed, thereby improving the reaction efficiency. Any organic solvent can be added in an arbitrary amount as far as is consistent with the enzymatic actions and effective to improve the solubility of isoflavone glycosides. Ethanol, methanol, acetone or dimethyl sulfoxide can be used for example. The pH of the reaction system is not limited either, unless the enzymes are inactivated. A preferred pH range is from 2 to 9. In using an acid protease preparation, a pH range of 3 to 5 is preferred.

The enzymatic reaction can be regarded completed when a sampled aliquot of the reaction mixture shows conversion of 90% or more of the isoflavone glycosides into the corresponding aglycones. On completion of the reaction, the reaction mixture is adjusted to pH 2 to 5, and water-soluble components are removed by ultrafiltration, centrifugal separation or a like technique to recover water-insoluble matter. If desired, the recovered water-insoluble matter is washed with water at pH 2 to 5. The separated water-soluble components (the soluble matter of the reaction mixture plus the washing) include water-solubilized amino acids and peptides resulting from decomposition by the protease and the sugar moieties resulting from hydrolysis by the β-glucosidase. Accordingly, the above operation removes components other than isoflavone aglycones and provides the insoluble matter enriched in aglycones.

A general process according to the present invention will be described hereunder for illustrative purposes only but not for limitation.

The above-described soybean raw material can be treated as such or, for facilitating the enzymes' reacting, previously reduced to powder in a grinder, etc. It is recommended to previously subject the raw material to heat treatment at 80 to 200° C. for about 10 to 60 minutes to deactivate nutrition inhibitory factors such as soybean trypsin inhibitor thereby facilitating the protease reaction.

An enzyme preparation having protease activity and β-glucosidase activity is then made to act on the soybean raw material. The enzyme preparation is used as dispersed in water beforehand. An organic solvent, such as ethanol, may be added to the enzyme dispersion in an amount of 1 to 50% by weight so as to improve the solubility of isoflavone glycosides. The soybean raw material is added to the enzyme dispersion prepared in a reactor whose temperature can be maintained constant, and the mixture is stirred to carry out enzyme reaction. Alternatively, water is added to the soybean raw material, and the enzyme preparation is added thereto, followed by stirring to conduct the reaction.

The pH and the temperature of the enzyme reaction system are adjusted to the optimum to ensure efficient progress of the enzyme reaction.

After confirming that 90% or more of the isoflavone glycosides in the reaction mixture has converted to the corresponding aglycones, the reaction mixture is adjusted to pH 2 to 5, and water-soluble components are removed by ultrafiltration, centrifugal separation or a like technique to recover water-insoluble matter. If desired, the recovered water-insoluble matter is washed with water at pH 2 to 5. The resulting wet solid is dried by means of, for example, a vacuum drier and pulverized to obtain an isoflavone aglycone-containing composition. Rich in isoflavone aglycones, the resulting powder can be utilized as health foods and general beverages and foodstuffs. The resulting powder or an intermediate product obtained in the course of the above-mentioned preparation process may be purified by organic solvent extraction or by use of a resin to provide high purity isoflavone aglycone preparations, which can be used as health foods, cosmetics or ingredients of pharmaceutical preparations.

The present invention will further be illustrated in greater detail with reference to Examples, but it should be understood that the invention is not construed as being limited thereto. Unless otherwise noted, all the percents are by weight.

EXAMPLE 1

Defatted soybeans (200 g) were ground and extracted with 1000 ml of 80% ethanol to obtain 23 g of an extract containing isoflavone glycosides. To the extract was added 500 ml of water to dissolve the extract. The solution was adjusted to pH 4.5, 2 g of Sumizyme FP (available from Shin-nihon Kagaku Kogyo K.K.) was added thereto, and the mixture was stirred at 55° C. overnight. It was found that 90% or more of the isoflavone glycosides had been converted to aglycones. The reaction mixture was adjusted to pH 4 with hydrochloric acid to precipitate an isoflavone fraction, which was collected by filtration. The filter cake was dissolved in 1000 ml of 0.1N NAOH, adjusted to pH 8, and passed through an activated carbon column. After washing the column with water, the adsorbed isoflavone aglycones were eluted with 2000 ml of 0.1N NaOH. The eluate was adjusted to pH 4.5 with hydrochloric acid to precipitate the aglycones, which were collected by filtration and dried in a vacuum drier to give 300 mg of an isoflavone aglycone powder having a purity of 70%. The isoflavone aglycone content of the resulting powder was found made up of 58% of genistein, 38% of daidzein, and 4% of glycitein, proving to be a composition mainly comprising genirstein. The analysis of the aglycone composition was in accordance with H. Wang et a l., *J. Agric. Food Chem.,* vol. 42, p. 666 (1994).

EXAMPLE 2

Three liters of water was added to 100 g of a commercially available soy protein isolate Fuji Pro F (available from Fuji Oil Co., Ltd.), and the mixture was heated in a boiling water bath for 10 minutes. After cooling, 10 g of Molsin F (available from Kikkoman Corp.) and 300 ml of ethanol were added thereto at a temperature kept at 50° C., followed by stirring at pH 5 overnight (16 hours). After the reaction, 95% or more of the isoflavones in the reaction mixture were found to have been converted to the corresponding aglycones. The reaction mixture was adjusted to a pH of 4.5. The precipitate was collected by centrifugation, washed with water at pH 4.5, and dried in a freeze-drier to obtain a product weighing 34 g. The product was found to have an isoflavone aglycone content of about 0.61%, which is about three times that of the raw material. Analysis by high-performance liquid chromatography revealed that the isoflavone aglycone composition of the product was made up of 56% of genistein, 39% of daidzein, and 5% of glycitein, proving to comprise genistein as a main aglycone.

EXAMPLE 3

To 1 kg of a commercially available isoflavone glycoside Novasoy (available from Archer Daniels Midland Co.) was added 25 l of distilled water. After the mixture was adjusted to pH 4.5 with hydrochloric acid, 150 g of Molsin F (Kikkoman Corp.) was added thereto, followed by stirring at 60° C. overnight (16 hours). After the reaction, 95% or more of the isoflavones in the reaction mixture were found converted to aglycones. The reaction mixture was adjusted to a pH of 2.5 with hydrochloric acid to precipitate an isoflavone fraction, which was washed with water at pH 2.5 and collected by filtration. The filter cake was stirred in 25 l of 90% ethanol for 2 hours to extract the isoflavones. The insoluble enzyme component was removed, the separated ethanol extract was concentrated, and the concentrate was spray-dried to obtain 480 g of an isoflavone aglycone powder. The resulting powder had an isoflavone aglycone content of 52%, which was found to be made up of 54% of genistein, 40% of daidzein, and 6% of glycitein, proving to comprise genistein as a main aglycone.

What is claimed is:

1. A process for producing an isoflavone aglycone-containing composition comprising allowing a protease and β-glucosidase to act on a soy protein raw material, an extract of a soy protein raw material or a by-product of a soy protein raw material to water-solubilize the protein of soybean origin and to convert isoflavone glycosides to the corresponding aglycones in an enzymatic reaction mixture, separating water-soluble components from the enzymatic reaction mixture, and recovering water-soluble matter comprising isoflavone aglycones, wherein a majority of said isoflavone aglycones is genistein.

2. The process according to claim 1, wherein said protease and said β-glucosidase are in the form of an enzyme preparation having both protease activity and β-glucosidase activity.

3. The process according to claim 2, wherein said protease and said β-glucosidase are acid enzymes the optimum pH of which is from 2.0 to 6.0.

4. The process according to claim 2, wherein said protease and said β-glucosidase are thermostable enzymes the optimum temperature of which is 50° C. or higher.

5. The process according to claim 1, wherein said soy protein raw material is at least one of whole soybeans, dehulled soybeans and defatted soybeans.

6. The process according to claim 1, wherein said extract of a soy protein raw material is at least one of a soy protein isolate, a soy protein concentrate, soybean milk, and a soybean extract containing isoflavone glycosides.

7. The process according to claim 1, wherein said by-product of a soy protein raw material is at least one of soybean molasses, soybean whey, and soybean curd waste.

8. The process according to claim 1, wherein the enzymatic reaction mixture contains 1 to 50% by weight of an organic solvent.

9. The process according to claim 1, wherein said protease and said β-glucosidase are acid enzymes the optimum pH of which is from 2.0 to 6.0.

10. The process according to claim 1, wherein said protease and said β-glucosidase are thermostable enzymes the optimum temperature of which is 50° C. or higher.

\* \* \* \* \*